US010676518B1

United States Patent
Lasalde-Dominicci et al.

(10) Patent No.: US 10,676,518 B1
(45) Date of Patent: Jun. 9, 2020

(54) A4B2 NICOTINIC ACETYLCHOLINE RECEPTORS WITH REDUCED OR INCREASED NICOTINE SENSITIVITY AND TRANSGENIC MOUSE MODEL FOR THE SAME

(71) Applicants: Jose A Lasalde-Dominicci, San Juan, PR (US); Nilza M Biaggi-Labiosa, San Juan, PR (US); Emir Aviles-Pagan, San Juan, PR (US); Daniel Caballero-Rivera, San Juan, PR (US)

(72) Inventors: Jose A Lasalde-Dominicci, San Juan, PR (US); Nilza M Biaggi-Labiosa, San Juan, PR (US); Emir Aviles-Pagan, San Juan, PR (US); Daniel Caballero-Rivera, San Juan, PR (US)

(73) Assignee: University of Puerto Rico, San Juan, PR (US)

( * ) Notice: Subject to any disclaimer, the term of this patent is extended or adjusted under 35 U.S.C. 154(b) by 0 days.

(21) Appl. No.: 15/141,689

(22) Filed: Apr. 28, 2016

Related U.S. Application Data

(60) Provisional application No. 62/153,660, filed on Apr. 28, 2015.

(51) Int. Cl.
  *C07K 14/705* (2006.01)
  *A01K 67/027* (2006.01)

(52) U.S. Cl.
  CPC .... *C07K 14/70571* (2013.01); *A01K 67/0275* (2013.01); *A01K 2217/054* (2013.01); *A01K 2227/105* (2013.01); *A01K 2267/03* (2013.01)

(58) Field of Classification Search
  CPC .......... C07K 14/70571; A01K 67/0275; A01K 2267/03; A01K 2227/105; A01K 2217/054
  See application file for complete search history.

(56) References Cited

U.S. PATENT DOCUMENTS

2009/0100532 A1* 4/2009 Drenan ............. A01K 67/0275
800/3

OTHER PUBLICATIONS

Gaj et al. Trends in Technology 31(7):397-405, Jul. 2013 (Year: 2013).*
Lilico et al. Scientific Reports 3: Article No. 2847. Dio:10.1038/srep02847. pp. 1-4, Oct. 10, 2013 (Year: 2013).*
Carlson et al. PNAS 109(43):17382-17387, Oct. 2012 (Year: 2012).*
Ji et al. Transgenic Res. 24:227-235, 2015 (Year: 2015).*
Liable et al. Biotechnology Journal 10:109-120, 2015 (Year: 2015).*
Haruyama et al. Curr Protoc Cel Biol. Mar. 2009. Chapter Unit-19.10. doi:10.1002/0471143030.cb11910s42. pp. 1-12 (Year: 2009).*
Roberts et al. Development 141:715-724, 2014 (Year: 2014).*
Ruan et al. Scientific Reports 5:14253, DIO:10.1038/srep14253, pp. 1-10, 2015 (Year: 2015).*
Leslie et al. Molecular Pharmacology 83:753-758, 2013. (Year: 2013).*

* cited by examiner

*Primary Examiner* — Ruixiang Li
(74) *Attorney, Agent, or Firm* — Hoglund & Pamias, PSC; Roberto J. Rios

(57) ABSTRACT

The α4β2 neuronal nicotinic acetylcholine receptor (nAChR) plays a crucial role in nicotine addiction. The invention studied the effect of subunit phosphorylation on α4β2 nAChR function and expression, and eleven residues located in the M3-M4 cytoplasmic loop were mutated to alanine and aspartic acid. When nicotine was used as an agonist, four mutations exhibited a statistically significant hypersensitivity to nicotine (S438D, S469A, Y576A, and S589A). Additionally, two mutations (S516D and T536A) that displayed normal activation with ACh displayed remarkable reductions in sensitivity to nicotine. The invention provides a knock-in mutant construct for the development of a transgenic mouse line with reduced nicotine sensitivity to be used in future studies.

2 Claims, 10 Drawing Sheets

Specification includes a Sequence Listing.

Fig. 10

A4B2 NICOTINIC ACETYLCHOLINE RECEPTORS WITH REDUCED OR INCREASED NICOTINE SENSITIVITY AND TRANSGENIC MOUSE MODEL FOR THE SAME

GOVERNMENT INTEREST

The claimed invention was made with U.S. Government support under grant numbers R25 GM061151 and P20 GM103642 awarded by the National Institutes of Health (NIH). The government has certain rights in this invention.

SEQUENCE LISTING

The instant application contains a Sequence Listing which has been submitted electronically in ASCII format and is hereby incorporated by reference in its entirety. Said ASCII copy, created on Feb. 16, 2018, is named UPR-15238_SL.txt and is 7,473 bytes in size.

BACKGROUND OF THE INVENTION

Neuronal nicotinic acetylcholine receptors (nAChRs) are transmitted gated ion channels that belong to a gene super family of homologous receptors including γ-aminobutyric acid (GABA), glycine, and serotonin receptors. The receptor is composed of five subunits with each having four transmembrane domains (M1-M4) and a large intracellular loop (C2). The genes for the subunits that have been cloned so far are divided into two subfamilies of nine α (α2-α10) and three β (β2-β4) subunits, and are expressed in the nervous system, cochlea, and a number of non-neuronal tissues.

Neuronal nAChRs have a role in the mediation of tolerance and addiction to nicotine in chronic tobacco users and the symptoms of withdrawal experienced upon cessation of use. The complex activities of nicotine in the nervous system are due to its ability to mimic the activity of acetylcholine (ACh) on these receptors. At the molecular level, chronic nicotine exposure differentially affects the number (up-regulation), subunit composition, stoichiometry, and functional status (desensitization and inactivation) of some nAChR subtypes, leaving others substantially unaffected. Nicotine, the addictive component of tobacco, has a predominant effect in the brain mainly on the α4β2 nAChR, the most abundant subtype.

Desensitization and up-regulation of nAChRs is thought to involve phosphorylation mediated by various kinases. For instance, protein kinase A (PKA) and protein kinase C (PKC) are examples of kinases that have been studied in the context of nAChR desensitization and up-regulation. Specifically, studies suggest that in the continuous presence of nicotine, receptors would be driven into inactive/desensitized conformations, a process likely influenced by the level of phosphorylation. There is evidence that activators of PKA and PKC increase nAChR binding sites and synergistically enhance nicotine-induced receptor up-regulation. These findings are validated by in vitro and in vivo studies, which have demonstrated that α4 nAChR subunits are phosphorylated and, more specifically, that they are targets of PKA phosphorylation. Studies using phosphopeptide mapping have provided evidence that residues S365, S472, and S491 of the rat α4 subunit, corresponding to positions S364, S471 and S490 on the current α4 NCBI reference sequence, are substrates for PKA phosphorylation. In addition, a recent study identified two major substrate sites for PKA phosphorylation on the human α4 subunit, namely S467 and S362, which are homologues to rat α4 positions S471 and S364 used in the current study.

Recent work from the inventors has shown that two-point mutations of a PKC phosphorylation residue, S336A and S336D, exhibit constitutive up-regulation when expressed in oocytes. In addition, we found that both of these PKC mutations changed the ACh affinity but exhibited no change in nicotine affinity, suggesting that the properties of agonist binding for α4β2 channel activation have very distinct dynamic and/or structural requirements for ACh and nicotine.

SUMMARY OF THE INVENTION

On the basis of these findings, we examined various consensus positions in the M3-M4 cytoplasmic loop of the α4 subunit in an attempt to dissect the potential role of this domain in the functional response of the α4β2 nAChR. This domain contains conserved consensus sites for various protein kinases (PKA, PKC, CKII, and TK) and has been recently mentioned as a possible target for allosteric sites. In the present study, eleven of these sites were mutated, to alanine and aspartic acid, to study the effect of α4 subunit phosphorylation on the α4β2 nAChR activation and expression. The rationale for using alanine and aspartic acid substitutions is that alanine impairs phosphorylation, whereas aspartic acid mimics phosphorylation of the protein. We used ACh and nicotine as agonists to test the functionality of the mutations as compared with the wild-type receptor. The present results reveal a novel allosteric linkage between the M3-M4 cytoplasmic loop of the α4 neuronal nAChR subunit that can regulate an agonist's selectivity and functional expression. This domain could be considered as a structural target for the development of smoking cessation drugs given that point mutations at this domain can decreased nicotine sensitivity.

BRIEF DESCRIPTION OF THE DRAWINGS

Further features and advantages of the invention will become apparent from the following detailed description taken in conjunction with the accompanying figures showing illustrative embodiments of the invention, in which:

FIG. 10 shows the consensus phosphorylation sites for the rat α4 M3/M4 intracellular domain.

Figure 1:
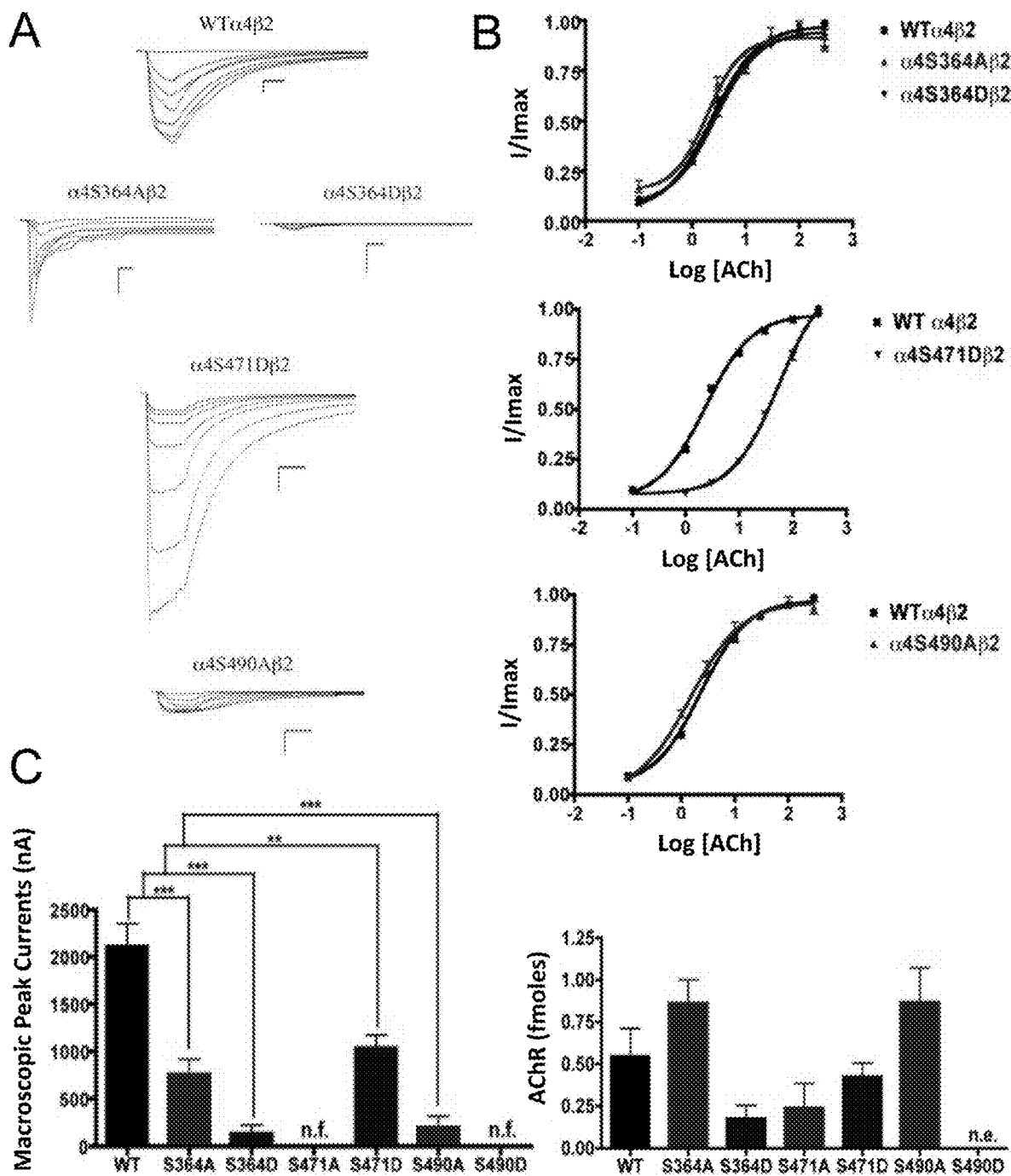
FIG. 1 shows the binding and functional characterization of mutations on PKA putative sites in the α4 subunit.

The Figure discloses SEQ ID NOS 1-3, respectively, in order of appearance.

DETAILED DESCRIPTION OF THE INVENTION

Materials and Methods
Site-Directed Mutagenesis

Single point mutations were prepared using the Quickchange™ Site-Directed Mutagenesis Kit (Stratagene, La Jolla, Calif.). The template used for the PCR reaction was the pGEMHE vector with Rattus norvegicus cDNA coding for the α4 neuronal nAChR subunit. DNA was purified using a QIAprep spin miniprep kit (Quiagen, Germantown, Md.) and then sequenced to confirm the incorporation of each mutation. A total of 11 residues in the cytoplasmic loop of the α4 subunit were chosen to be mutated: S364, T417, S438, S469, S471, S490, S504, S516, T536, Y576, and S589. Each residue was mutated to alanine (A) and aspartic acid (D).

In Vitro Synthesis of mRNA and Oocyte Microinjection

Each subunit encoding mRNA was synthesized in vitro from linearized pGEMHE plasmid templates of Rattus norvegicus cDNA coding for α4 and β2 nAChR subunits using the mMessage mMachine RNA transcription kit (Ambion, Austin, Tex.). mRNA mixtures of α4 and β2 subunits were prepared at 2 μg:3 μg ratio, and 32.2 nL of this mixture was microinjected into each oocyte. The mRNA mixture was microinjected, using a displacement injector (Drummond Instruments, Broomhall, Pa.), into stage V and VI oocytes that had been extracted, incubated in collagenase Type 1A (Sigma, St. Louis, Mo.), and defolliculated by manual dissection. The injected oocytes were incubated at 19° C. for 3-4 days in ND-96 medium supplemented with albumin, gentamicin, tetracycline, and theophyline. Electrophysiological experiments were performed after the third or fourth day of mRNA injection.

Electrophysiological Characterization of α4β2 nAChRs

Oocytes injected with the mRNA transcripts of α4 and β2 subunits were characterized using a two-electrode voltage clamp. ACh- and nicotine-induced currents were recorded at 20° C., 3-4 days after mRNA injection, with a GeneClamp 500B Amplifier (Axon Instruments, Foster City, Calif.). Electrodes were filled with 3M KCl and had a resistance of less than 5 megaohms. Impaled oocytes in the recording chamber were continuously perfused at a rate of 5 ml/min with MOR-2 buffer (115 mM NaCl, 2.5 mM KCl, 5 mM HEPES, 1 mM $Na_2HPO_4$, 0.2 mM $CaCl_2$, 5 mM $MgCl_2$, and 0.5 mM EGTA, pH 7.4). All the reagents used were purchased from Sigma-Aldrich, Co. (St. Louis, Mo.). For dose-response curves, each oocyte was held at a membrane potential of −70 mV. Membrane currents were digitized using the DigiData 1322A interface (Axon Instruments, Foster City, Calif.), filtered at 2 kHz during recording. The Clampex 10.0 software running on a Pentium 4-based computer was used for data acquisition. Data analysis was via Prism 3.0 (Graphpad Software, San Diego, Calif.). Dose-response data for the α4β2 combination were collected using seven ACh doses (0.1, 1, 3, 10, 30, 100, and a seventh concentration ranging from 300 to 1000 μM depending on the mutant) and seven nicotine concentrations (0.1, 1, 3, 10, 30, 100, 300 μM). The data were fitted using a one-component sigmoidal dose-response equation, $Y=I/I_{max}$Bottom+$(I/I_{max}$Top−$I/I_{max}$Bottom$)/(1+10\hat{\ }((\log EC_{50}-X)\times$Hill-Slope)) where X is the logarithm of concentration and Y is the response.

Epibatidine Binding Assays $^{125}$I-labeled epibatidine (PerkinElmer Life Sciences, Boston, Mass.) binding assays were performed to determine membrane expression of nAChR in oocytes. The oocytes were incubated in 50 pM $^{125}$I-labeled epibatidine with 5 mg/mL albumin serum bovine in MOR-2 without EGTA at room temperature for 2 h. Non-injected oocytes were also incubated in $^{125}$I-labeled epibatidine to measure nonspecific binding (PerkinElmer 2470 WIZARD Gamma Counter). Excess epibatidine was removed by washing each oocyte with 60 mL of MOR-2 without EGTA. A standard linear regression was obtained by plotting the counts per minute (CPM) against $^{125}$I-labeled epibatidine concentration (0.5-20 fmol).

Determination in Potential Changes in Subunit Stoichiometry of α4β2 nAChRs Using A-85380

To determine whether the α4β2 mutations α4S469Aβ2, α4S471Dβ2, α4T536Aβ2 and α4Y576Aβ2 expressed in Xenopus laevis oocytes assemble in the α4(2):β2(3) or the α4(3):β2(2) stoichiometry, we estimated the efficacy of agonist A-85380 when compared to ACh 300 μM. The α4(2):β2(3) stoichiometry was favored by microinjecting α4β2 mRNA in a 1:10 ratio, and the α4(3):β2(2) by microinjecting in a 10:1 ratio. The efficacy of A-85380 in WTα4(2):β2(3) and WTα4(3):β2(1) was determined by comparing the macroscopic current elicited by A-85380 100 nM and ACh 300 μM in oocytes microinjected α4β2 mRNA in 1:10 and 10:1 ratios, respectively. The efficacy of A-85380 in α4S469Aβ2, α4S471Dβ2, α4T536Aβ2 and α4Y576Aβ2 was determined by comparing the macroscopic current elicited by A-85380 100 nM and ACh 300 μM in oocytes microinjected α4β2 mRNA in 2:3 ratio. The changes in stoichiometry in these four mutants were assessed by comparing the efficacy of A-85380 in each mutant compared to WTα4(2):β2(3) and WTα4(3):β2(2).

Results

Functional Effects of Mutations at PKA Putative Phosphorylation Sites in the α4 Subunit when Using ACh as an Agonist Mutations α4S364A, α4S364D, α4S471D, and α4S490A resulted in receptors with a significant decrease in macroscopic peak current as compared with the wild-type (WT) receptor as shown in FIG. 1. This figure shows the binding and functional characterization of mutations on PKA putative sites in the α4 subunit. Voltage-clamp recordings were used to determine the macroscopic response of mutations α4S364Aβ2, α4S364Dβ2, α4S471Aβ2, α4S471Dβ2, α4S490Aβ2, α4S490Dβ2 and wild-type α4β2 nAChRs expressed in Xenopus laevis oocytes to several ACh and nicotine concentrations. (A) Family of ACh-induced macroscopic currents. Calibration bars are shown for all family of currents, horizontal bars indicate time (5 s) and vertical bars indicate the inward current (500 nA). (B) Dose-response relationships obtained by voltage-clamp using ACh as an agonist. ACh dose-response curves were determined using seven ACh concentrations (0.1, 1, 3, 10, 30, 100, and a seventh concentration ranging from 300 to 1000 μM depending on the mutant). The responses were normalized to the maximum response (I/Imax). (C) Left panel, comparison of the macroscopic peak currents of all the mutations and wild-type receptor shown in nA. Right panel, results of the $^{125}$I-labeled epibatidine binding experiments performed in Xenopus laevis oocytes expressing the mutations α4S364Aβ2, α4S364Dβ2, α4S471Aβ2, α4S471Dβ2, α4S490Aβ2, α4S490Dβ2 and wild-type α4β2 nAChRs shown in fmoles (n=6-17) (* p<0.0005,  p<0.005).

Mutations α4S471A and α4S490D resulted in non-functional receptors. Statistical analysis using an unpaired t test showed no significant difference in the ACh $EC_{50}$ value between mutations α4S364A, α4S364D, α4S490A, and the WT α4β2 nAChR (2.55±0.08, 2.71±0.05, 1.51±0.08, and 2.33±0.03 μM, respectively). On the other hand, mutation α4S471D exhibited a significant $EC_{50}$ increase (i.e. 53.60±0.05 μM) as compared with the WT ACh $EC_{50}$ value, as shown in Table 1 below.

This mutation exhibited a significant decrease in the macroscopic peak current as compared with that of the WT receptor. The nicotine $EC_{50}$ values revealed no difference between the mutation and the WT receptor (Table 1). This was a remarkable observation as the α4S471D mutation shows a significant difference in ACh activation as compared with the WT; however, nicotine activation in this mutant was similar to that in the WT receptor. This kind of behavior was previously described in mutations of PKC residue S336.

TABLE 1

Electrophysiological characterization of α4β2 nAChR mutations reveal different nicotine and ACh sensitivities

| | | ACh | | | Nicotine | | |
|---|---|---|---|---|---|---|---|
| Kinase | Mutation | $EC_{50}$ (μM) | Hill Coef. | Peak Current (nA) | $EC_{50}$ (μM) | Hill Coef. | Peak Current (nA) |
| — | WT α4β2 | 2.33 ± 0.03 | 1.00 | 2110 ± 243 | 4.21 ± 0.41 | 1.80 | 387 ± 66 |
| PKA | α4S364Aβ2 | 2.55 ± 0.08 | 1.22 | 759 ± 157 | n/f | n/f | n/f |
| | α4S364Dβ2 | 2.71 ± 0.05 | 1.07 | 135 ± 87*** | n/f | n/f | n/f |
| | α4S471Aβ2 | n/f | n/f | n/f | n/f | n/f | n/f |
| | α4S471Dβ2 | 53.60 ± 0.05*** | 1.01 | 1039 ± 139** | 5.02 ± 0.62 | 2.00 | 142 ± 313** |
| | α4S490Aβ2 | 1.51 ± 0.08 | 0.91 | 200 ± 115*** | n/f | n/f | n/f |
| | α4S490Dβ2 | n/e | n/e | n/e | n/e | n/e | n/e |
| CKII | α4T417Aβ2 | 77.80 ± 0.12*** | 0.76 | 1557 ± 306 | 2.12 ± 0.61* | 1.33 | 293 ± 120 |
| | α4T417Dβ2 | 46.09 ± 0.05*** | 0.99 | 360 ± 89*** | 2.11 ± 0.32** | 1.78 | 582 ± 255 |
| | α4S438Aβ2 | 11.00 ± 0.19*** | 0.49 | 97 ± 29*** | n/f | n/f | n/f |
| | α4S438Dβ2‡ | 3.96 ± 0.09* | 0.68 | 1938 ± 367 | 2.17 ± 0.16** | 1.29 | 2156 ± 475** |
| | α4S469Aβ2‡ | 43.59 ± 0.09*** | 0.87 | 2222 ± 413 | 3.37 ± 0.20 | 1.84 | 1552 ± 313** |
| | α4S469Dβ2 | n/f | n/f | n/f | n/f | n/f | n/f |
| | α4S504Aβ2 | n/f | n/f | n/f | n/f | n/f | n/f |
| | α4S504Dβ2 | n/f | n/f | n/f | n/f | n/f | n/f |
| PKC | α4S516Aβ2 | 65.89 ± 0.06*** | 1.04 | 1027 ± 169*** | n/f | n/f | n/f |
| | α4S516Dβ2¶ | 43.72 ± 0.12*** | 0.79 | 3296 ± 581 | 3.80 ± 0.68 | 1.48 | 76 ± 16*** |
| | α4T536Aβ2¶ | 38.25 ± 0.11*** | 0.67 | 3345 ± 129*** | 3.84 ± 0.61 | 1.80 | 110 ± 28*** |
| | α4T536Dβ2 | 85 ± 17*** | 0.69 | 216 ± 85*** | n/f | n/f | n/f |
| | α4S589Aβ2‡ | 77 ± 10*** | 0.80 | 1644 ± 192 | 4.67 ± 0.56 | 1.61 | 1882 ± 672* |
| | α4S589Dβ2 | n/f | n/f | n/f | n/f | n/f | n/f |
| TK | α4Y576Aβ2‡ | 55 ± 8*** | 0.91 | 4398 ± 450*** | 3.76 ± 0.60 | 1.65 | 874 ± 221* |
| | α4Y576Dβ2 | 35 ± 7*** | 0.62 | 396 ± 65*** | n/f | n/f | n/f |

Mutations highlighted in green (‡) exhibit hypersensitivity to nicotine while those in red (¶) exhibit agonist selectivity evidenced by their remarkable reductions in sensitivity to nicotine.
Legend:
(n/f) non-functional;
(n/e) no-expression;
Error estimates are expressed as the mean ± SEM of 6-17 oocytes. *P <0.05, P <0.005, *P <0.0005

Functional Effects of Mutations at PKA Putative Phosphorylation Sites in the α4 Subunit when Using Nicotine as an Agonist.

Figure 2:
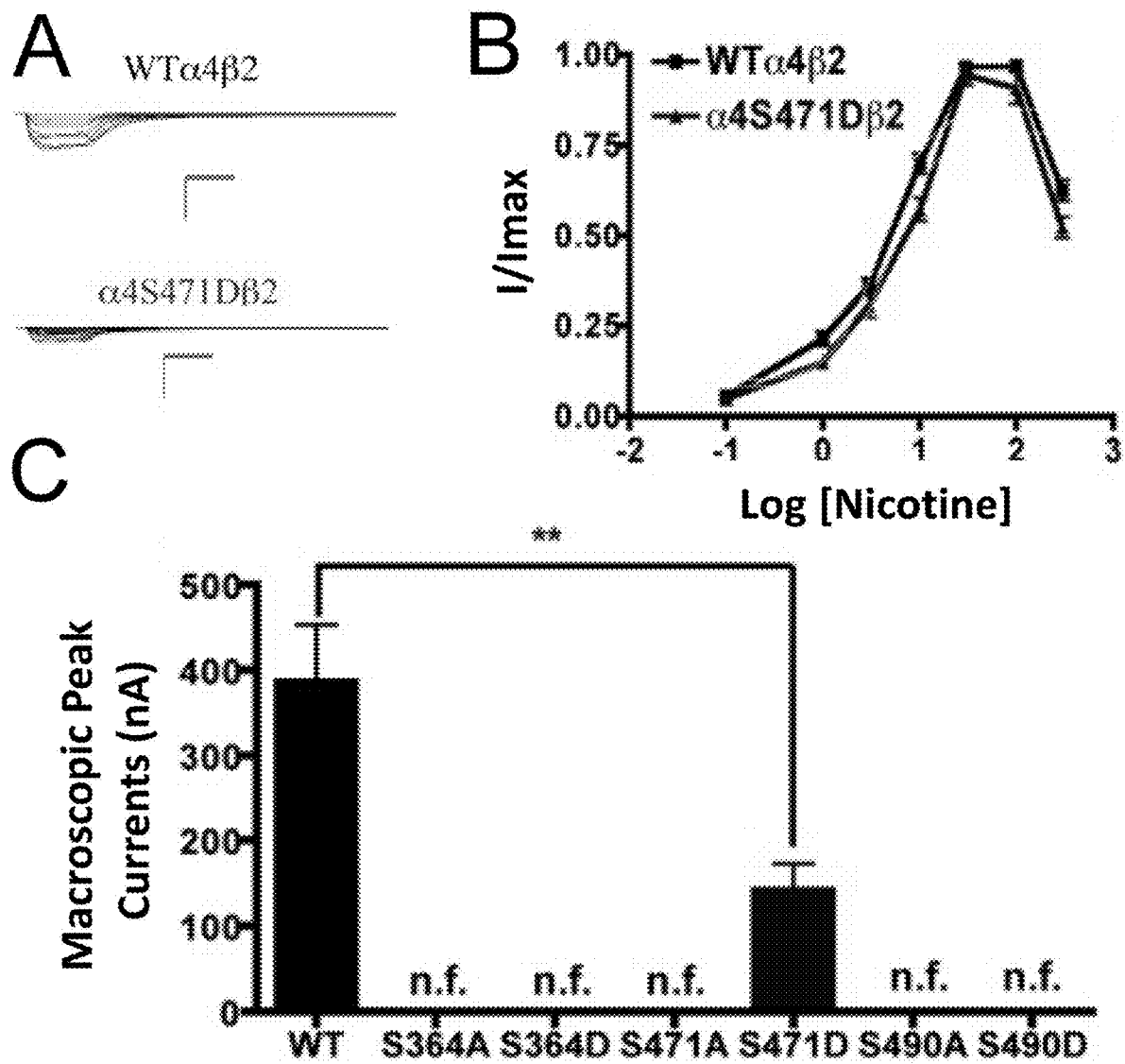
FIG. 2 shows the functional characterization of mutations on PKA putative sites in the α4 subunit with nicotine used as agonist.

All of the PKA mutants were studied with the use of nicotine as an agonist. The only mutation that exhibited functional activation by nicotine was α4S471D, as shown in FIG. 2. This figure shows the functional characterization of mutations on PKA putative sites in the α4 subunit with nicotine used as agonist. (A) Family of nicotine-induced macroscopic currents for mutation α4S471Dβ2 and the wild-type α4β2 nAChR. Calibration bars are shown for all family of currents, horizontal bars indicate time (5 s) and vertical bars indicate the inward current (500 nA). (B) Dose-response relationships obtained by voltage-clamp using nicotine as agonist. Nicotine dose-response curves were determined using seven nicotine concentrations (0.1, 1, 3, 10, 30, 100 and 300 μM). The responses were normalized to the maximum response (I/Imax). (C) Comparison of the nicotine-induced macroscopic peak currents of the mutations and wild-type receptor shown in nA (n=6-17) (** p<0.005).

Effects on nAChR Expression of Mutations at PKA Putative Phosphorylation Sites in the α4 Subunit $^{125}$I-labeled epibatidine binding assays revealed the expression patterns of the various mutations of PKA residues in the α4 subunit (FIG. 1C, right panel). Statistical analysis using an unpaired t test revealed no significant changes among any of the mutations as compared with the WT nAChR. Although mutation α4S490D did not exhibit any function during the voltage-clamp experiments (Table 1), it was still subjected to the binding assays which revealed no expression for mutation α4S490D.

Figure 3:
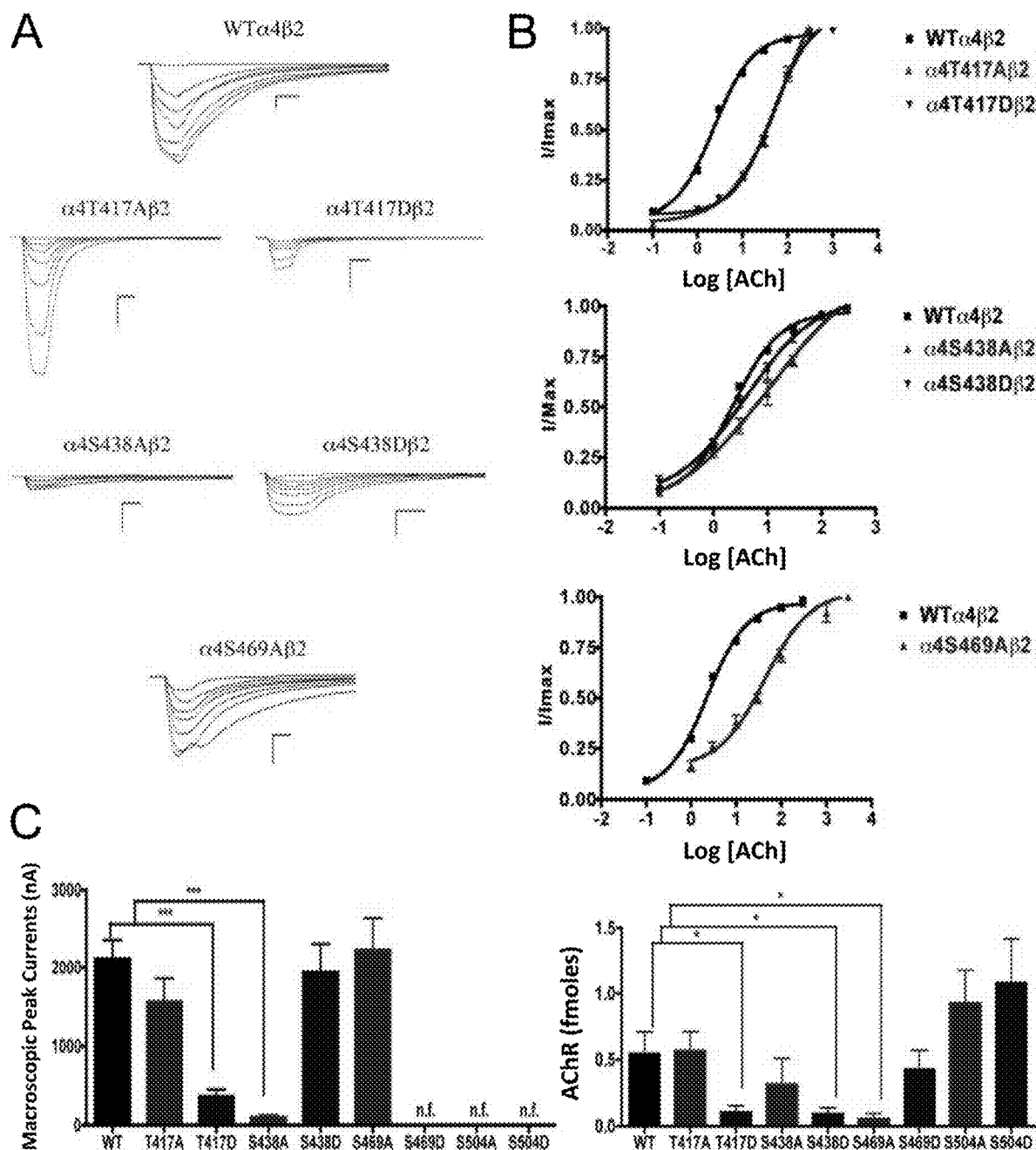
FIG. 3 shows the binding and functional characterization of mutations on CKII putative phosphorylation sites in the α4 subunit with ACh used as an agonist.

Functional Effects of Mutations at CKII Putative Phosphorylation Sites in the α4 Subunit when Using ACh as an Agonist Voltage-clamp data analysis revealed significant decreases in the macroscopic peak currents for mutations α4T417D and α4S438A, as shown in FIG. 3. This figure shows the binding and functional characterization of mutations on CKII putative phosphorylation sites in the α4 subunit with ACh used as an agonist. Mutations α4T417Aβ2, α4T417Dβ2, α4S438Aβ2, α4S438Dβ2, α4S469Aβ2, α4S469Dβ2, α4S504Aβ2, and α4S504Dβ2 were expressed in *Xenopus laevis* oocytes. (A) Family of ACh-induced macroscopic currents. Calibration bars are shown for all family of currents, horizontal bars indicate time (5 s) and vertical bars indicate the inward current (500 nA). (B) Dose-response curves obtained by voltage-clamp using ACh as agonist. ACh dose-response curves were determined using seven ACh concentrations (0.1, 1, 3, 10, 30, 100, and a seventh concentration ranging from 300 to 1000 μM depending on the mutant). The responses were normalized to the maximum response (I/Imax). (C) Left panel. Comparison of the macroscopic peak currents of all the mutations compared with the wild-type receptor, shown in nA. Right panel. Results of the $^{125}$I-labeled epibatidine binding experiments performed in *Xenopus laevis* oocytes expressing the mutations α4T417Aβ2, α4T417Dβ2, α4S438Aβ2, α4S438Dβ2, α4S469Aβ2, α4S469Dβ2, α4S504Aβ2, and α4S504Dβ2 and wild-type α4β2 nAChRs, shown in fmoles (n=6-17) (* p<0.05, ***p<0.0001).

On the other hand, mutations α4T417A, α4S438D, and α4S469A showed no change in the macroscopic peak current (Table 1). At the same time, mutations α4S469D, α4S504A, and α4S504D resulted in non-functional receptors. The ACh $EC_{50}$ values for all of the functional mutations of the CKII putative sites α4T417A, α4T417D, α4S438A, α4S438D, and α4S469A resulted in significant increases when compared with the WT nAChR (Table 1).

Figure 4:
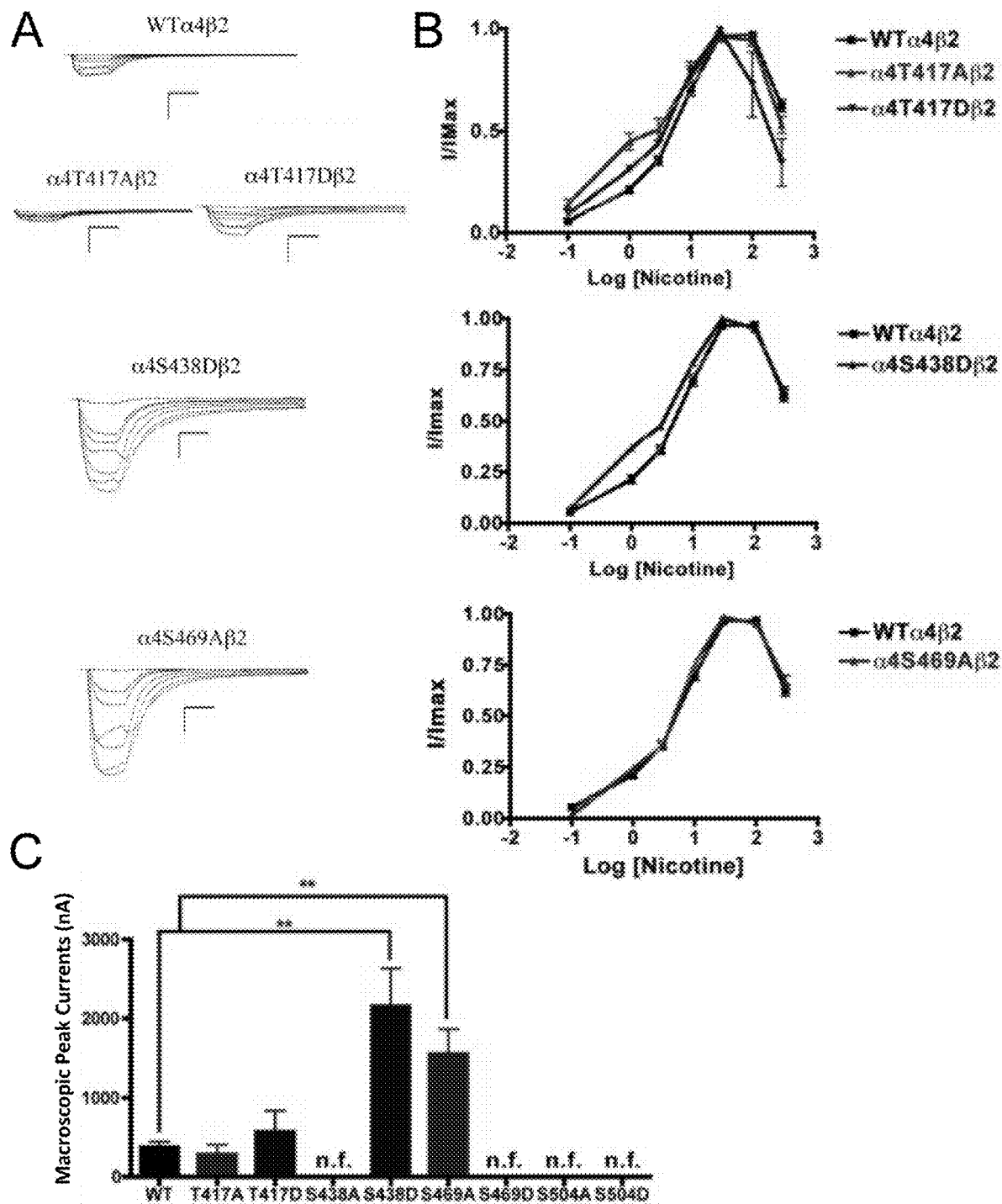
FIG. 4 shows the functional characterization of mutations on CKII putative phosphorylation sites in the α4 subunit with nicotine used as agonist.

Functional Effects of Mutations at CKII Putative Phosphorylation Sites in the α4 Subunit when Using Nicotine as an Agonist When nicotine was used as agonist, we found that mutations α4S469D, α4S504A, and α4S504D also resulted in non-functional receptors. However, although mutation α4S438A was a functional receptor when ACh was used as agonist, it resulted in a non-functional receptor when nicotine was used as an agonist. Mutations of residue α4T417 exhibited no significant change in macroscopic current when compared with the WT receptor; however, their nicotine $EC_{50}$ values decreased significantly, as shown in FIG. 4. This figure shows the functional characterization of mutations on CKII putative phosphorylation sites in the α4 subunit with nicotine used as agonist. Voltage-clamp recordings were used to determine the macroscopic response to several nicotine concentrations of mutations of CKII putative sites and wild-type α4β2 nAChRs expressed in *Xenopus laevis* oocytes. (A) Family of nicotine-induced macroscopic currents for mutations α4T417Aβ2, α4T417Dβ2, α4S438Dβ2, α4S469Aβ2, and the wild-type α4β2 nAChR. Calibration bars are shown for all family of currents, horizontal bars indicate time (5 s) and vertical bars indicate the inward current (500 nA). (B) Dose-response relationships obtained by voltage-clamp experiments with nicotine used as an agonist. Nicotine dose-response curves were determined using seven nicotine concentrations (0.1, 1, 3, 10, 30, 100, and 300 μM). The responses were normalized to the maximum response (I/Imax). (C) Comparison of the nicotine-induced macroscopic peak currents of the mutations and wild-type receptor, shown in nA (n=6-17) (**p<0.005).

These mutations displayed a higher potency for nicotine. Interestingly, mutations α4S438D and α4S469A exhibited significant increases in the macroscopic peak currents (2156±475 and 1552±313 nA, respectively) when compared with the WT receptor (387±66 nA) (Table 1). The nicotine $EC_{50}$ value for α4S438D exhibited a significant decrease whereas mutation α4S469A exhibited no change. These results suggest that mutations α4S438D and α4S469A enhance the sensitivity to nicotine.

Effects on nAChR Expression of Mutations at CKII Putative Phosphorylation Sites in the α4 Subunit.

$^{125}$I-labeled epibatidine binding assays on mutations of the CKII residues revealed significant decreases in receptor expression for mutations α4T417D, α4S438D, and α4S469A (FIG. 3C, right panel). On the other hand, mutations α4T417A and α4S438A did not exhibit changes in expression when compared with the WT receptor. More interestingly, three mutations that resulted in non-functional receptors when using ACh and nicotine (α4S469D, α4S504A, and α4S504D) exhibited no change in receptor expression (FIG. 3C right panel, and Table 1).

Figure 5:
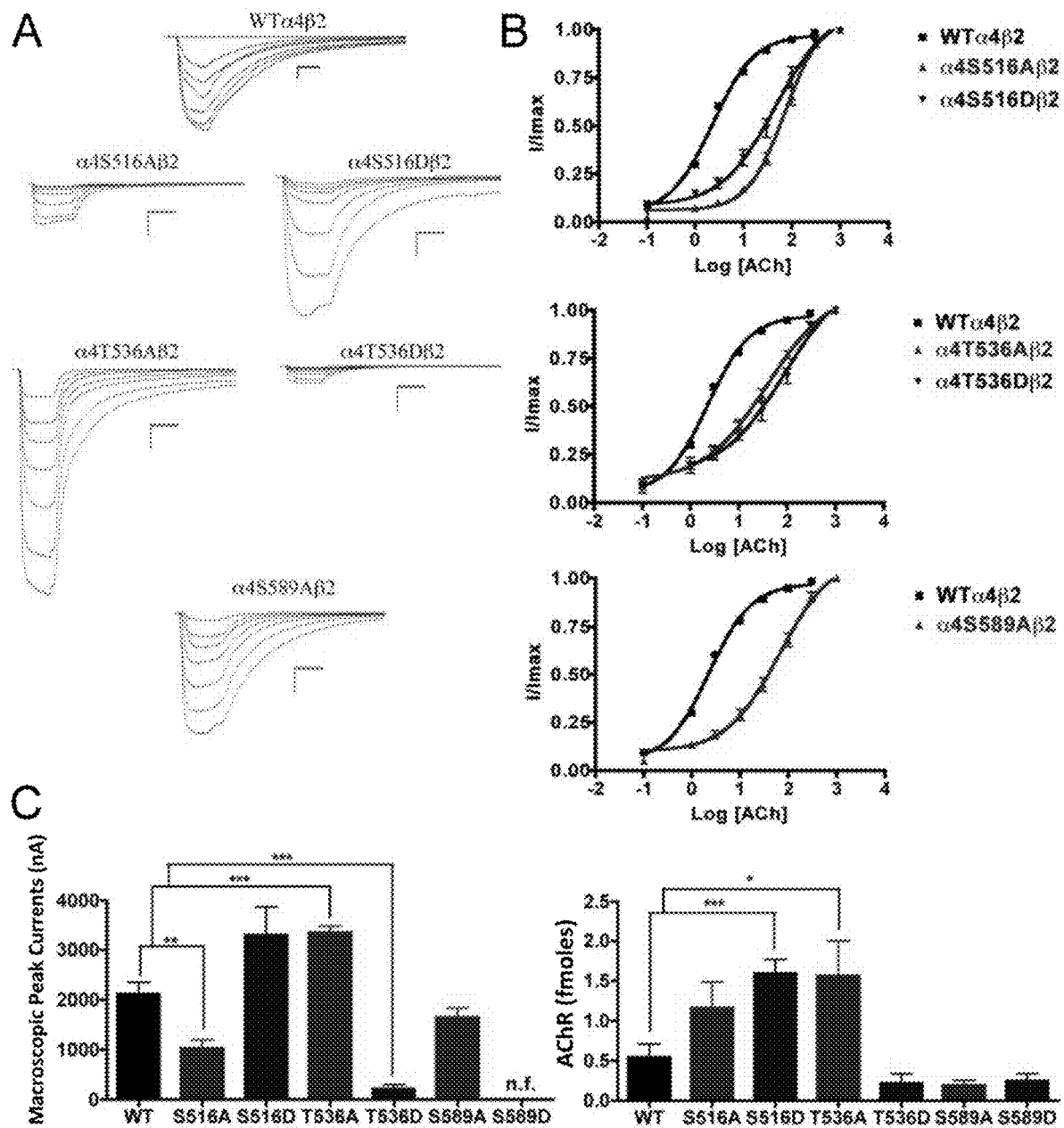
FIG. 5 shows the binding and functional characterization of mutations on PKC putative phosphorylation sites in the α4 subunit with ACh used as an agonist.

Functional Effects of Mutations at PKC Putative Phosphorylation Sites in the α4 Subunit when Using ACh as an Agonist The alanine substitution at position α4S516 displayed a significant decrease in macroscopic peak current (1027±169 nA), as shown in FIG. 5. This figure shows the binding and functional characterization of mutations on PKC putative phosphorylation sites in the α4 subunit with ACh used as an agonist. Mutations α4S516Aβ2, α4S516Dβ2, α4T536Aβ2, α4T536Dβ2, α4S589Aβ2, and α4S589Dβ2 were expressed in *Xenopus laevis* oocytes. (A) Family of ACh-induced macroscopic currents. Calibration bars are shown for all family of currents, horizontal bars indicate time (5 s) and vertical bars indicate the inward current (500 nA). (B) Dose-response curves obtained by voltage-clamp experiments with ACh used as an agonist. ACh dose-response curves were determined using seven ACh concentrations (0.1, 1, 3, 10, 30, 100, and a seventh concentration ranging from 300 to 1000 μM depending on the mutant). The responses were normalized to the maximum response (I/Imax). (C) Left panel. Comparison of the macroscopic peak currents of all the mutations compared with the wild-type receptor shown in nA. Right panel. Results of the $^{125}$I-labeled epibatidine binding experiments performed in *Xenopus laevis* oocytes expressing the mutations α4S516Aβ2, α4S516Dβ2, α4T536Aβ2, α4T536Dβ2, α4S589Aβ2, and α4S589Dβ2 and wild-type α4β2 nAChRs, shown in fmoles (n=6-17) (*p<0.05, p<0.005, *p<0.0005).

Mutation α4T536A showed a significant increase in macroscopic peak current (3345±129 nA), whereas mutation α4T536D showed a significant decrease in macroscopic peak current (216±85 nA) when compared with the WT receptor (Table 1). Mutation α4S589A displayed a functional receptor with no change in macroscopic peak current (1644±192 nA) when compared with the WT receptor. However, mutating the same residue to aspartic acid, α4S589D, resulted in a non-functional receptor (i.e., no significant current was detected). The five mutations that exhibited functional channels (α4S516A, α4S516D, α4T536A, α4T536D, and α4S589A) exhibited a significant increase in the ACh $EC_{50}$ value as compared with the WT receptor (Table 1).

Figure 6:
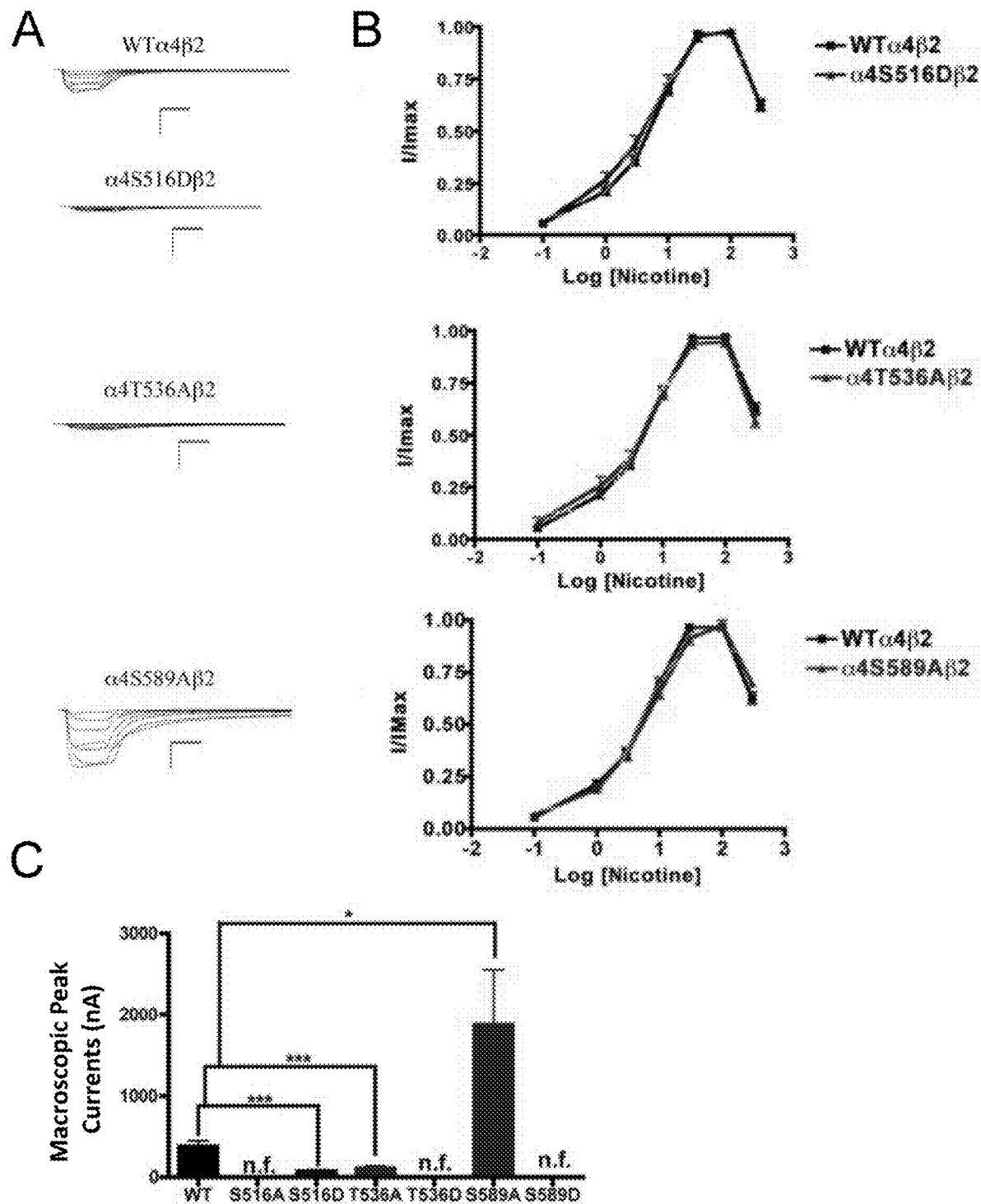
FIG. 6 shows the functional characterization of mutations on PKC putative phosphorylation sites in the α4 subunit with nicotine used as an agonist.

Functional Effects of Mutations at PKC Putative Phosphorylation Sites in the α4 Subunit when Using Nicotine as an Agonist We performed voltage-clamp experiments on the mutations of PKC putative sites, this time using nicotine as an agonist. Mutations α4S516A, α4T536D, and α4S589D exhibited no nicotine-induced currents, an unsurprising outcome given that their response to ACh was significantly decreased. However, mutations α4S516D and α4T536A exhibited extremely low nicotine-induced currents, as shown in FIG. 6. This figure shows the functional characterization of mutations on PKC putative phosphorylation sites in the α4 subunit with nicotine used as an agonist. Voltage-clamp recordings were used to determine the macroscopic response to several nicotine concentrations of mutations of PKC putative sites and wild-type α4β2 nAChRs expressed in *Xenopus laevis* oocytes. (A) Family of nicotine-induced macroscopic currents for the mutations and the wild-type α4β2 nAChR. Calibration bars are shown for all family of currents, horizontal bars indicate time (5 s) and vertical bars indicate the inward current (500 nA). (B) Dose-response relationships obtained by voltage-clamp experiments with nicotine used as an agonist. Nicotine dose-response curves were determined using seven nicotine concentrations (0.1, 1, 3, 10, 30, 100, and 300 µM). The responses were normalized to the maximum response (I/Imax). (C) Comparison of the nicotine-induced macroscopic peak currents, shown in nA (n=6-17) (*p<0.05, ***p<0.0005).

This was an interesting finding because both of these mutations exhibited either no change (α4S516D) or an increase (α4T536A) in the ACh-induced macroscopic peak current. On the other hand, mutation α4S589A displayed a significant increase in macroscopic peak current, while exhibiting no change in the nicotine $EC_{50}$ value (Table 1).

Effects on nAChR Expression of Mutations at PKC Putative Phosphorylation Sites in the α4 Subunit The binding assays, using $^{125}$I-labeled epibatidine, to measure receptor expression showed significant increases in receptor expression when compared with the WT receptor. Mutations α4S516D, and α4T536A showed significant increases in receptor expression when compared with the WT α4β2 nAChR (FIG. 5C, right panel). These mutations resulted in receptors that are constitutively up-regulated. Mutation α4S589D displayed a behavior similar to that seen previously in mutations α4S504A and α4S504D; it showed no signs of ACh- and nicotine-induced macroscopic currents (Table 1). However, binding assays revealed no change in receptor expression for mutation α4S589D when compared with the WT receptor (FIG. 5C, right panel).

Functional Effects of Mutations of a TK Putative Phosphorylation Site in the α4 Subunit when Using ACh as an Agonist.

Figure 7:
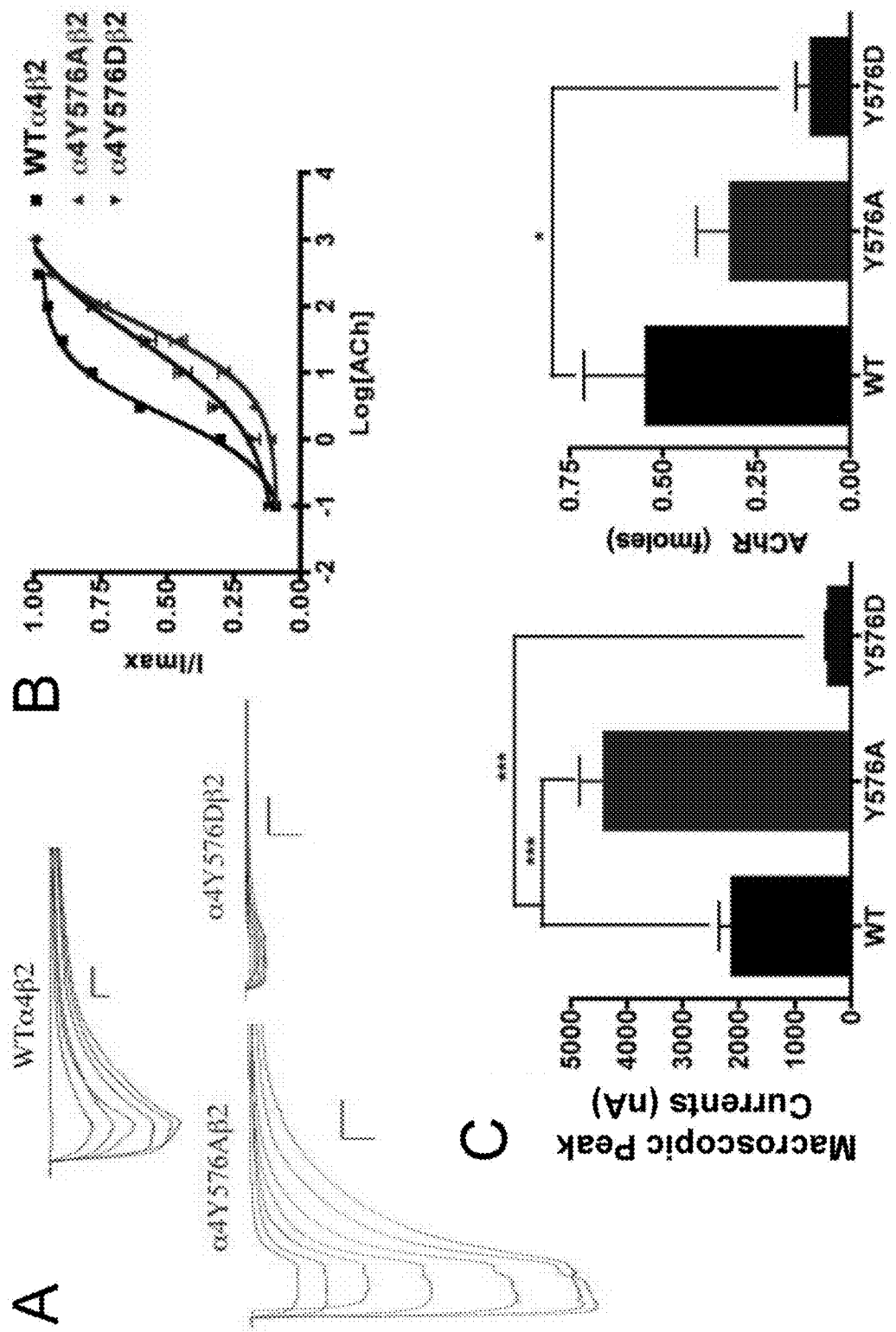
FIG. 7 shows the binding and functional characterization of mutations on the TK putative phosphorylation site in the α4 subunit with ACh used as an agonist.

The alanine substitution in the TK putative site α4Y576 exhibited a significant increase in the macroscopic peak current (4398±450 nA), and the aspartic acid substitution resulted in a significant decrease in macroscopic peak current (396±65 nA) when compared with the α4β2 nAChR as shown in FIG. 7. This figure shows the binding and functional characterization of mutations on the TK putative phosphorylation site in the α4 subunit with ACh used as an agonist. Mutations α4Y576Aβ2 and α4Y576Dβ2 were expressed in *Xenopus laevis* oocytes. (A) Family of ACh-induced macroscopic currents. Calibration bars are shown for all family of currents, horizontal bars indicate time (5 s) and vertical bars indicate the inward current (500 nA). (B) Dose-response curves obtained by voltage-clamp experiments with ACh used as an agonist. ACh dose-response curves were determined using seven ACh concentrations (0.1, 1, 3, 10, 30, 100, and a seventh concentration ranging from 300 to 1000 µM depending on the mutant). The responses were normalized to the maximum response (I/Imax). (C) Left panel. Comparison of the macroscopic peak currents of all the mutations compared with the wild-type receptor, shown in nA. Right panel. Results of the $^{125}$I-labeled epibatidine binding experiments performed in *Xenopus laevis* oocytes expressing the mutations α4Y576Aβ2 and α4Y576Dβ2 and wild-type α4β2 nAChRs, shown in fmoles (n=6-17) (*p<0.05, ***p<0.0005).

The ACh $EC_{50}$ values for α4Y576A (55±8 µM) and for α4Y576D (35±7 µM) increased significantly when compared with the WT receptor, which has an $EC_{50}$ value of 2.33±0.03 µM (Table 1). These increases in ACh $EC_{50}$ values have also been seen in other mutations.

Figure 8:
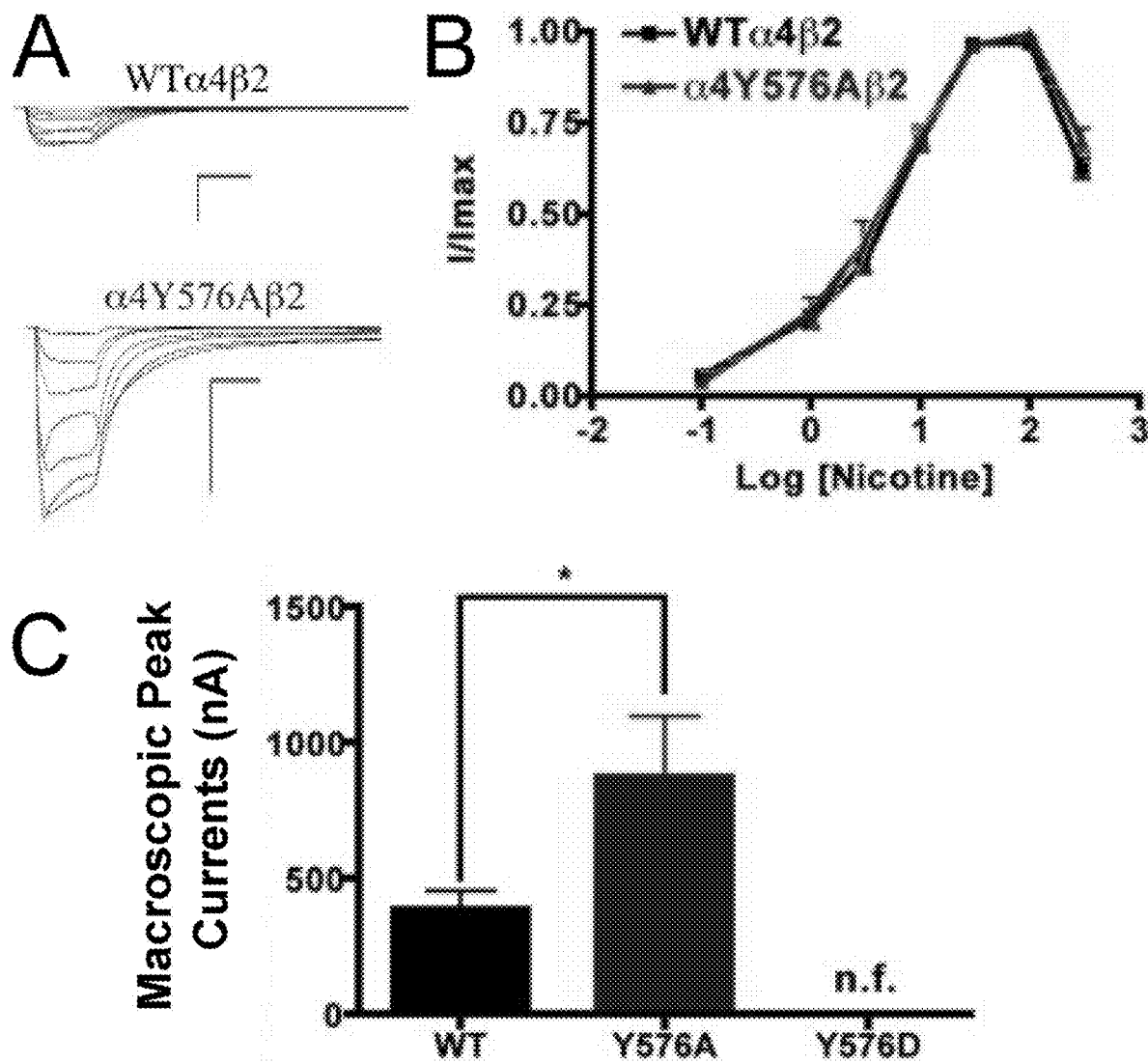
FIG. 8 shows the functional characterization of mutations on the TK putative phosphorylation site in the α4 subunit with nicotine used as an agonist.

Functional Effects of Mutations of a TK Putative Phosphorylation Site in the α4 Subunit when Using Nicotine as an Agonist Mutation α4Y576A exhibited a significant increase in the macroscopic peak current whereas mutation α4Y576D exhibited no significant nicotine-induced current, resulting in a non-functional channel, as shown in FIG. 8. The figure shows the functional characterization of mutations on the TK putative phosphorylation site in the α4 subunit with nicotine used as an agonist. Voltage-clamp recordings were used to determine the macroscopic response to several nicotine concentrations of mutations of TK putative sites and wild-type α4β2 nAChRs expressed in *Xenopus laevis* oocytes. (A) Family of nicotine-induced macroscopic currents for mutation α4Y576Aβ2 and the wild-type α4β2 nAChR. Calibration bars are shown for all family of currents, horizontal bars indicate time (5 s) and vertical bars indicate the inward current (500 nA). (B) Dose-response relationships obtained by voltage-clamp experiments with nicotine used as an agonist. Nicotine dose-response curves were determined using seven nicotine concentrations (0.1, 1, 3, 10, 30, 100, and 300 µM). The responses were normalized to the maximum response (I/Imax). (C) Comparison of the nicotine-induced macroscopic peak currents, shown in nA (n=6-17) (*p<0.05).

Since mutation α4Y576D exhibited a significant decrease in the ACh-induced macroscopic peak current, it was not surprising that there was no significant nicotine-induced current. The nicotine $EC_{50}$ value for mutation α4Y576A revealed no significant difference when compared with the WT receptor (Table 1). Our data indicate that mutation α4Y576A exhibits an enhanced sensitivity to nicotine.

Effects on nAChR Expression of Mutations of TK Putative Phosphorylation Sites in the α4 Subunit The results of the binding assays performed on mutations α4Y576A and α4Y576D revealed that only mutation α4Y576D decreased receptor expression significantly, whereas mutation α4Y576A saw no change in receptor expression when compared with the α4β2 nAChR (FIG. 7C, right panel).

DISCUSSION

Functional Implications of PKA Consensus Phosphorylation Residues in the α4 Subunit: Possible Inhibitory Role for PKA Residues.

PKA mutants that expressed functional receptors displayed significant decreases in macroscopic current, whereas receptor expression was unchanged. These results indicate that assembly of the α4β2 nAChR was unaffected by PKA mutations while receptor function was significantly decreased. Also, when ACh was used in mutation α4S364A, it displayed faster decay rates as compared with WT. This result suggests that a residue far away from the binding site of the α4 subunit can affect agonist association and channel activation and inactivation kinetics via a complex network of allosteric interactions.

The mutant α4S490D resulted in no measurable expression levels suggesting that phosphorylation of this residue shuts down α4β2 nAChR expression completely, by affecting trafficking or assembly. Thus, PKA residues may play an inhibitory role in vivo since the mutations mentioned above resulted in functional inhibition and, in one case, complete shutdown of α4β2 nAChR expression.

Figure 10:
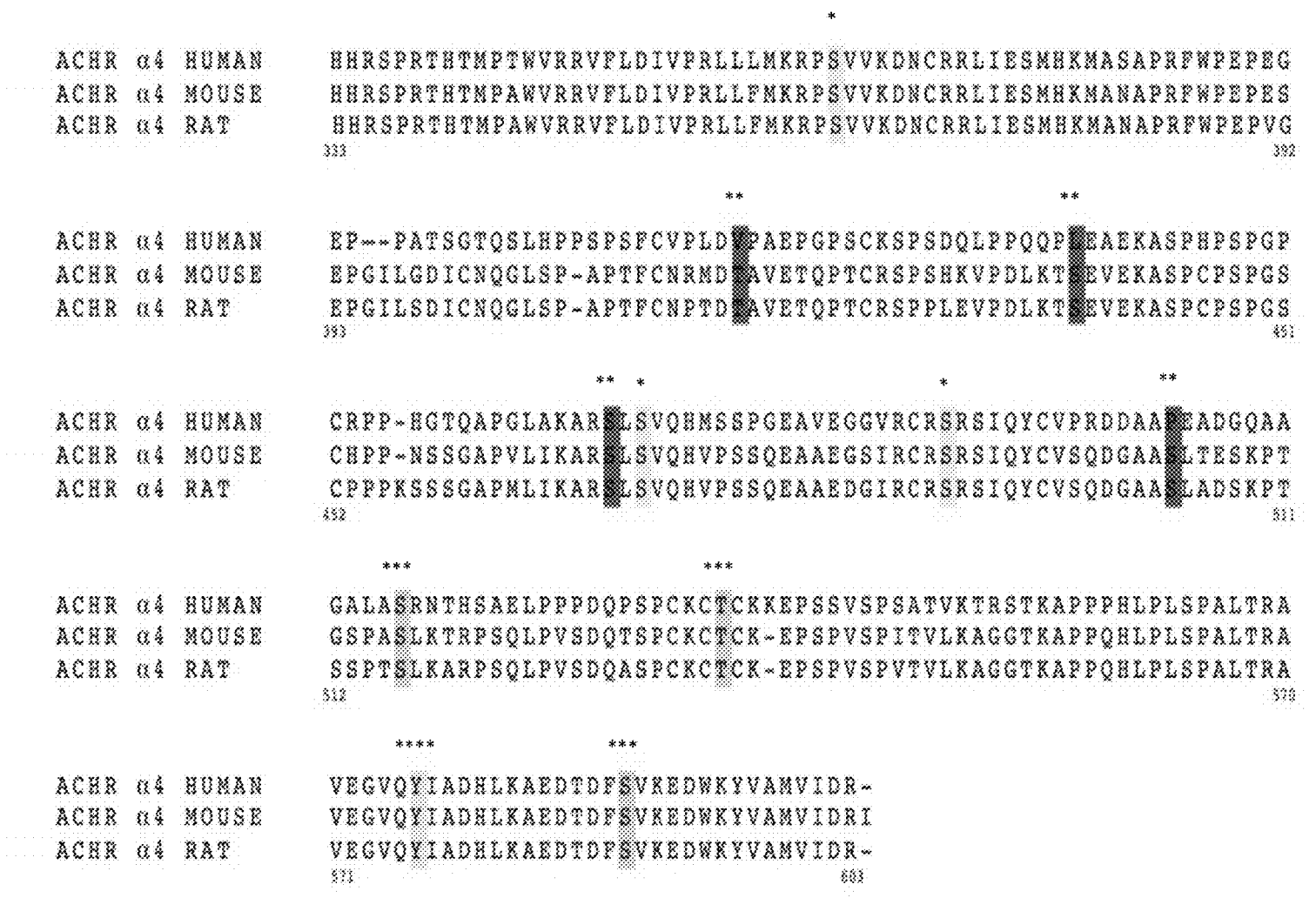

Functional Implications of CKII Consensus Phosphorylation Residues in the α4 Subunit: Possible Modulatory Role for CKII Residues Residues α4T417, α4S438, α4S469, and α4S504 may be phosphorylated by CKII due to their amino acid sequence, but they have not been extensively studied. We found that mutations in two of these positions, namely α4S438D and α4S469A, displayed significant increases in their nicotine-induced functional responses, whereas α4S438A and α4S469D exhibited no functional response to nicotine. These results suggest that a single mutation in the α4 intracellular domain can enhance nicotine sensitivity, and that consensus positions in the M3-M4 intracellular domain can influence the allosteric properties of α4β2. FIG. 10 shows the consensus phosphorylation sites for the rat α4 M3/M4 intracellular domain. Sequence alignment of the M3/M4 intracellular loop of the neuronal nAChR α4 subunit from different species. Consensus phosphorylation sites are highlighted in color according to the governing kinase: (*) yellow for protein kinase A (PKA), () red for casein kinase II (CKII), (*) green for protein kinase C (PKC) and (****) cyan for tyrosine kinase (TK). Furthermore, because α4S469A exhibited decreased potency for ACh but retained the same potency for nicotine as the WT receptor further demonstrates that nicotine and ACh have different requirements for channel activation. Since α4S469A exhibited an increase in peak currents to nicotine, this mutation could be a novel model for the study of nicotine tolerance. Interestingly, α4S469A results from the substitution of only one nucleotide and could, therefore, occur in vivo via a single nucleotide polymorphism (SNP) of CHRNA4.

Functional Implications of PKC Consensus Phosphorylation Residues in the α4 Subunit: PKC Residues May Regulate Agonist Activation and Up-Regulation It is known that PKC phosphorylates the α4 subunit, and studies using mutations of residues phosphorylated by PKC have demonstrated how phosphorylation affects receptor desensitization and up-regulation by chronic nicotine treatment. Two of the PKC mutations, α4S516D and α4T536A, resulted in an increase in receptor expression; no other kinase residue mutations exhibited this kind of behavior. Moreover, these two mutations exhibited either normal (α4S516D) or increased (α4T536A) functional activation by ACh. However, their response to nicotine was extremely reduced as compared with the WT. Moreover, the peak current elicited by a nicotine concentration found in a chronic smoker (i.e. 0.1 μM) was almost undetected (i.e. 5 nA for α4S516D and 6 nA for α4T536A). This finding is remarkable: two novel mutations, far from the binding site, that can influence agonist activation. These two mutations produced α4β2 nAChRs that can discriminate for nicotine activation without major effects on ACh activation. These mutations could provide a novel perspective for new therapies for smoking cessation—targeting a residue that can make α4β2 nAChRs insensitive to nicotine without major effects on normal AChR function. At the same time, mutation α4S589A exhibited an enhanced sensitivity to nicotine as evidenced by a significant increase in macroscopic peak current. This result is noteworthy in that the identification of a position along the α4 subunit cytoplasmic loop that influences nicotine sensitivity in the α4β2 receptor suggests that this domain could have a role in the design of novel smoking cessation drugs.

Binding assays revealed no change in receptor expression for mutation α4S589D when compared with WT. This result suggests that a negative charge at this position completely shuts down receptor function, regardless of receptor expression levels.

Functional Implications of the TK Consensus Phosphorylation Residue in the α4 Subunit: Possible Role for Regulating Nicotine Sensitivity and Expression Residue α4Y576 is proposed to be phosphorylated by tyrosine kinase. The present data suggest that TK sites may play a role in regulating receptor expression and nicotine sensitivity. We base this assumption on the fact that mutation α4Y576A exhibits an increase in the peak current to ACh and nicotine. Mutation α4Y576D exhibits a decrease in the functional activation by ACh, fails to respond to nicotine, and exhibits a decrease in receptor expression. These results suggest that phosphorylation at the α4Y576 consensus position down-regulates both receptor function and expression and support our hypothesis for a role for this TK site in regulating agonist sensitivity and receptor expression.

Changes in ACh Potency in the S469A, S471D, T536A and Y576A Mutations does not Involve Alterations in α4β2 nAChRs Subunit Stoichiometry.

Figure 9:
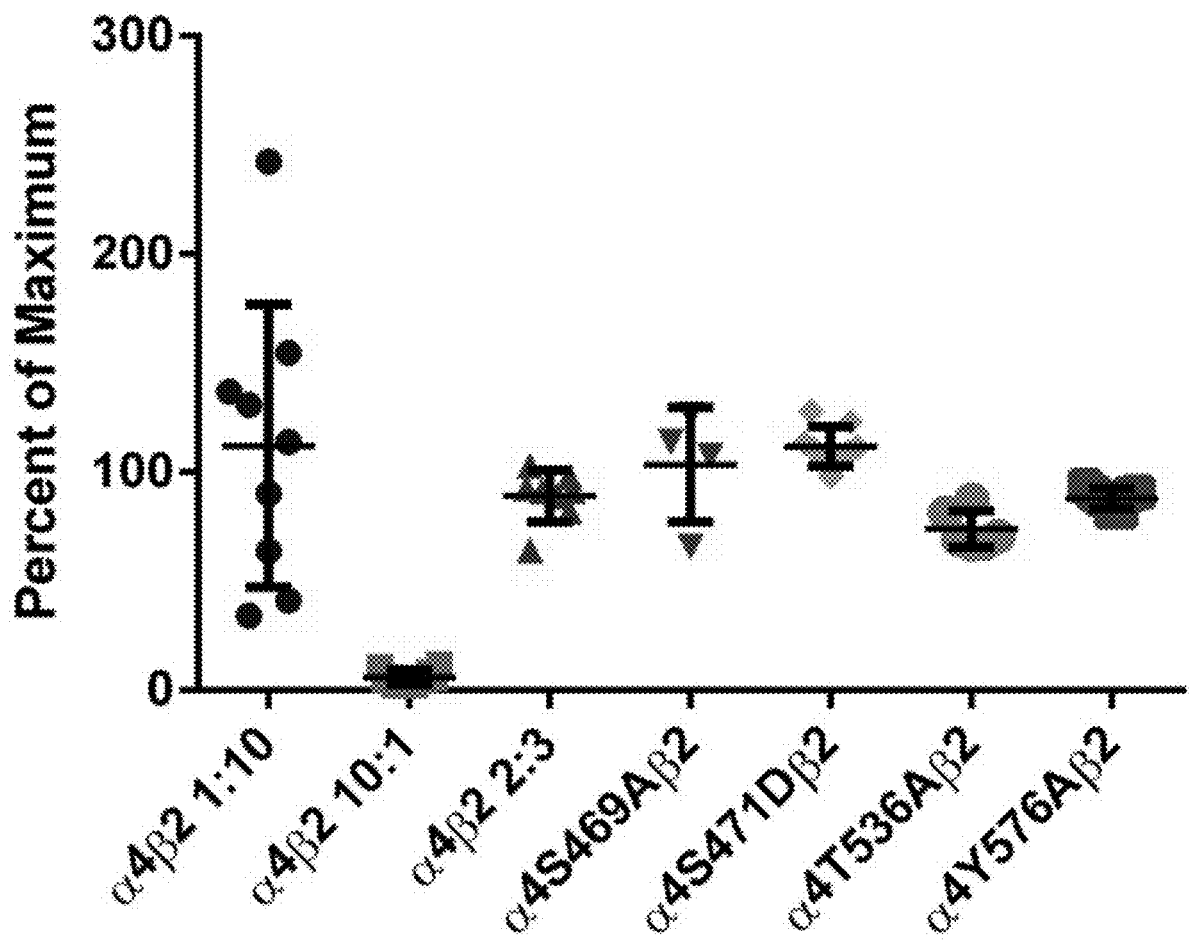
FIG. 9 shows the efficacy of α4β2 agonist A-85380 for stoichiometry determination.

The decrease in potency for ACh exhibited by the majority of the mutations suggests potential changes in α4β2 nAChR stoichiometry. Previous studies have shown that the α4(3):β2(2) stoichiometry has a characteristic lower affinity for ACh whereas the α4(2):β2(3) stoichiometry exhibits a higher affinity for ACh. Moreover, evidence suggests that phosphorylation of S467 (S471 in the present study) on free α4 subunits prior to their association with β2 subunits has long-lasting consequences, increasing the stability of the α4 subunits. This increase in stability may result in an enhanced expression of α4β2 in the low affinity α4(3):β2(2) configuration. However, as FIG. 9 suggests, the observed decrease in ACh potency cannot be explained by alterations in the α4(2):β2(3) stoichiometry. FIG. 9 shows the efficacy of α4β2 agonist A-85380 for stoichiometry determination. Oocytes were injected with α4β2 mRNA at either a ratio of 10:1, 1:10 or 2:3 for WTα4β2 and in a 2:3 ratio for α4 mutants α4S469Aβ2, α4S471Dβ2, α4T536Aβ2 and α4Y576Aβ2. Current was measure for 300 μM ACh and 100 nM A-85380. Efficacy was measured as the percent of maximum when compared to ACh. The efficacy was significantly lower in oocytes injected at a ratio of 10:1 than oocytes injected at a ratio of 1:10 (***p<0.0001). Oocytes injected at a 2:3 ratio show no significant difference from those injected at a 1:10 ratio. The four mutations show no significant difference from the WT injected 2:3 or 1:10 ratio, suggesting that the receptors maintain the same stoichiometry.

The efficacy of agonist A-85380 has been reported to be significantly reduced in the α4(3):β2(2) stoichiometry. The efficacy of A-85380 in α4β2 mutations S469A, S471D, T536A, and Y576A indicate that these are assembled according to the α4(2):β2(3) stoichiometry.

Researchers are mostly in the dark about the structure and functional role of the intracellular domain of the AChR. The present data suggest a role for the cytoplasmic loop of the α4 subunit in α4β2 function, expression, and agonist selectivity. Point mutations at consensus sites of the α4 nAChR subunit have remarkable effects on α4β2 function and expression (Table 1). More specifically, these mutations affect the activation properties of ACh and nicotine; however, it is difficult to confirm a role for phosphorylation from the mutations' effects alone. Since our data show that targeting residues 5516 and T536 can render α4β2 nAChRs almost insensitive to nicotine without major effects on normal AChR function, we propose that PKC could be a feasible target for smoking cessation drugs. Therefore, this invention provides the framework for further experiments with membrane-permeant cAMP analogs, antagonists, or other potential modulators of phosphorylation. Alternatively, it is possible that the mutations characterized in this study, besides affecting phosphorylation states, could also disrupt key point-to-point interactions essential for secondary structure and/or signal transduction. Twelve mutant receptors (S471A, S471D, T417A, S438A, S469D, S504A, S504D, S516A, T536D, S589A, S589D, and Y576A) exhibited significant changes in potency for ACh without affecting receptor expression levels.

We previously proposed a model that is consistent with an allosteric site for ACh activation, whereas nicotine activation displayed a biphasic curve. In the present invention, seven mutations displaced dose-response curves to higher ACh concentrations while displaying WT-like biphasic profiles for nicotine activation. Therefore, all of these mutations produced a negative allosteric effect on ACh activation without affecting the biphasic curve for nicotine activation. Furthermore, three other mutations showed only minor changes in the nicotine profile.

Overall, the effects that we observed in this study are fairly complex, for example, we observed decrease in peak response with both A and D mutations. In this particular case it is very likely that the mutation is not really mimicking a phosphorylation. Nonetheless, these results are consistent with previous reports of biphasic nicotine profiles for α4β2 nAChRs. Most important, we discovered mutations that can provide novel perspectives for the design of nicotine smoking cessation medications that do not act directly or indirectly on the agonist's binding site. The invention provides a α4T536A knock-in mutant construct for the development of a transgenic mouse line with reduced nicotine sensitivity to be used in future studies. Overall, these findings provide a new perspective for developing smoking cessation drugs that can definitely cause changes in the pharmacology of nicotinic receptors.

We claim:

1. A mutant nicotinic acetylcholine receptor comprising a point mutation of threonine (T) to alanine (A) in the M3-M4 cytoplasmic loop of alpha 4 subunit at position 536 corresponding to the amino acid residue position 202 of the amino acid sequence set forth in SEQ ID NO: 1, said mutant nicotinic acetylcholine receptor has reduced nicotine sensitivity.

2. A mutant nicotinic acetylcholine receptor comprising a point mutation of serine (S) to aspartic acid (D) in the M3-M4 cytoplasmic loop of the alpha 4 subunit at the position 516 corresponding to the amino acid residue position 182 of the amino acid sequence set forth in SEQ ID NO: 1, said mutant nicotinic acetylcholine receptor has reduced nicotine sensitivity.

* * * * *

SEQUENCE LISTING

<160> NUMBER OF SEQ ID NOS: 3

<210> SEQ ID NO 1
<211> LENGTH: 270
<212> TYPE: PRT
<213> ORGANISM: Homo sapiens

<400> SEQUENCE: 1

```
His His Arg Ser Pro Arg Thr His Thr Met Pro Thr Trp Val Arg Arg
1               5                   10                  15

Val Phe Leu Asp Ile Val Pro Arg Leu Leu Leu Met Lys Arg Pro Ser
            20                  25                  30

Val Val Lys Asp Asn Cys Arg Arg Leu Ile Glu Ser Met His Lys Met
        35                  40                  45

Ala Ser Ala Pro Arg Phe Trp Pro Glu Pro Gly Glu Pro Pro Ala
    50                  55                  60

Thr Ser Gly Thr Gln Ser Leu His Pro Pro Ser Pro Ser Phe Cys Val
65                  70                  75                  80

Pro Leu Asp Val Pro Ala Glu Pro Gly Pro Ser Cys Lys Ser Pro Ser
                85                  90                  95

Asp Gln Leu Pro Pro Gln Gln Pro Leu Glu Ala Glu Lys Ala Ser Pro
                100                 105                 110

His Pro Ser Pro Gly Pro Cys Arg Pro Pro His Gly Thr Gln Ala Pro
            115                 120                 125

Gly Leu Ala Lys Ala Arg Ser Leu Ser Val Gln His Met Ser Ser Pro
130                 135                 140

Gly Glu Ala Val Glu Gly Gly Val Arg Cys Arg Ser Arg Ser Ile Gln
145                 150                 155                 160

Tyr Cys Val Pro Arg Asp Asp Ala Ala Pro Glu Ala Asp Gly Gln Ala
                165                 170                 175

Ala Gly Ala Leu Ala Ser Arg Asn Thr His Ser Ala Glu Leu Pro Pro
            180                 185                 190

Pro Asp Gln Pro Ser Pro Cys Lys Cys Thr Cys Lys Lys Glu Pro Ser
        195                 200                 205

Ser Val Ser Pro Ser Ala Thr Val Lys Thr Arg Ser Thr Lys Ala Pro
    210                 215                 220

Pro Pro His Leu Pro Leu Ser Pro Ala Leu Thr Arg Ala Val Glu Gly
225                 230                 235                 240
```

Val Gln Tyr Ile Ala Asp His Leu Lys Ala Glu Asp Thr Asp Phe Ser
            245                 250                 255

Val Lys Glu Asp Trp Lys Tyr Val Ala Met Val Ile Asp Arg
            260                 265                 270

<210> SEQ ID NO 2
<211> LENGTH: 271
<212> TYPE: PRT
<213> ORGANISM: Mus musculus

<400> SEQUENCE: 2

His His Arg Ser Pro Arg Thr His Thr Met Pro Ala Trp Val Arg Arg
1               5                   10                  15

Val Phe Leu Asp Ile Val Pro Arg Leu Leu Phe Met Lys Arg Pro Ser
            20                  25                  30

Val Val Lys Asp Asn Cys Arg Arg Leu Ile Glu Ser Met His Lys Met
            35                  40                  45

Ala Asn Ala Pro Arg Phe Trp Pro Glu Pro Ser Glu Pro Gly Ile
    50                  55                  60

Leu Gly Asp Ile Cys Asn Gln Gly Leu Ser Pro Ala Pro Thr Phe Cys
65              70                  75                  80

Asn Arg Met Asp Thr Ala Val Glu Thr Gln Pro Thr Cys Arg Ser Pro
                85                  90                  95

Ser His Lys Val Pro Asp Leu Lys Thr Ser Glu Val Glu Lys Ala Ser
            100                 105                 110

Pro Cys Pro Ser Pro Gly Ser Cys His Pro Pro Asn Ser Ser Gly Ala
            115                 120                 125

Pro Val Leu Ile Lys Ala Arg Ser Leu Ser Val Gln His Val Pro Ser
            130                 135                 140

Ser Gln Glu Ala Ala Glu Gly Ser Ile Arg Cys Arg Ser Arg Ser Ile
145                 150                 155                 160

Gln Tyr Cys Val Ser Gln Asp Gly Ala Ala Ser Leu Thr Glu Ser Lys
                165                 170                 175

Pro Thr Gly Ser Pro Ala Ser Leu Lys Thr Arg Pro Ser Gln Leu Pro
            180                 185                 190

Val Ser Asp Gln Thr Ser Pro Cys Lys Cys Thr Cys Lys Glu Pro Ser
            195                 200                 205

Pro Val Ser Pro Ile Thr Val Leu Lys Ala Gly Gly Thr Lys Ala Pro
            210                 215                 220

Pro Gln His Leu Pro Leu Ser Pro Ala Leu Thr Arg Ala Val Glu Gly
225                 230                 235                 240

Val Gln Tyr Ile Ala Asp His Leu Lys Ala Glu Asp Thr Asp Phe Ser
            245                 250                 255

Val Lys Glu Asp Trp Lys Tyr Val Ala Met Val Ile Asp Arg Ile
            260                 265                 270

<210> SEQ ID NO 3
<211> LENGTH: 271
<212> TYPE: PRT
<213> ORGANISM: Rattus norvegicus

<400> SEQUENCE: 3

His His Arg Ser Pro Arg Thr His Thr Met Pro Ala Trp Val Arg Arg
1               5                   10                  15

Val Phe Leu Asp Ile Val Pro Arg Leu Leu Phe Met Lys Arg Pro Ser
            20                  25                  30

```
Val Val Lys Asp Asn Cys Arg Arg Leu Ile Glu Ser Met His Lys Met
    35              40                  45
Ala Asn Ala Pro Arg Phe Trp Pro Glu Pro Val Gly Glu Pro Gly Ile
    50              55                  60
Leu Ser Asp Ile Cys Asn Gln Gly Leu Ser Pro Ala Pro Thr Phe Cys
65              70              75                          80
Asn Pro Thr Asp Thr Ala Val Glu Thr Gln Pro Thr Cys Arg Ser Pro
            85                  90                  95
Pro Leu Glu Val Pro Asp Leu Lys Thr Ser Glu Val Glu Lys Ala Ser
            100             105                 110
Pro Cys Pro Ser Pro Gly Ser Cys Pro Pro Lys Ser Ser Ser Gly
            115             120             125
Ala Pro Met Leu Ile Lys Ala Arg Ser Leu Ser Val Gln His Val Pro
            130             135             140
Ser Ser Gln Glu Ala Ala Glu Asp Gly Ile Arg Cys Arg Ser Arg Ser
145             150             155                 160
Ile Gln Tyr Cys Val Ser Gln Asp Gly Ala Ala Ser Leu Ala Asp Ser
                165             170             175
Lys Pro Thr Ser Ser Pro Thr Ser Leu Lys Ala Arg Pro Ser Gln Leu
            180             185             190
Pro Val Ser Asp Gln Ala Ser Pro Cys Lys Cys Thr Cys Lys Glu Pro
            195             200             205
Ser Pro Val Ser Pro Val Thr Val Leu Lys Ala Gly Gly Thr Lys Ala
    210             215             220
Pro Pro Gln His Leu Pro Leu Ser Pro Ala Leu Thr Arg Ala Val Glu
225             230             235             240
Gly Val Gln Tyr Ile Ala Asp His Leu Lys Ala Glu Asp Thr Asp Phe
                245             250             255
Ser Val Lys Glu Asp Trp Lys Tyr Val Ala Met Val Ile Asp Arg
            260             265             270
```